United States Patent
Alland et al.

(10) Patent No.: US 9,708,671 B2
(45) Date of Patent: Jul. 18, 2017

(54) **DETECTION OF DRUG RESISTANT *MYCOBACTERIUM TUBERCULOSIS***

(71) Applicant: Rutgers, The State University of New Jersey, New Brunswick, NJ (US)

(72) Inventors: David Alland, Bernardsville, NJ (US); Soumitesh Chakravorty, Somerset, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 327 days.

(21) Appl. No.: 14/391,437

(22) PCT Filed: Apr. 10, 2013

(86) PCT No.: PCT/US2013/035985
§ 371 (c)(1),
(2) Date: Oct. 9, 2014

(87) PCT Pub. No.: WO2013/155189
PCT Pub. Date: Oct. 17, 2013

(65) Prior Publication Data
US 2015/0079589 A1    Mar. 19, 2015

Related U.S. Application Data

(60) Provisional application No. 61/622,403, filed on Apr. 10, 2012.

(51) Int. Cl.
*C12Q 1/68* (2006.01)

(52) U.S. Cl.
CPC ....... *C12Q 1/689* (2013.01); *C12Q 2600/156* (2013.01)

(58) Field of Classification Search
None
See application file for complete search history.

(56) References Cited

U.S. PATENT DOCUMENTS 7,445,895 B2    11/2008    Chou et al.

FOREIGN PATENT DOCUMENTS

WO    2011140237 A2    11/2011

OTHER PUBLICATIONS

Chakravorty et al. Rapid detection of fluoroquinolone-resistant and heteroresistant *Mycobacterium tuberculosis* by use of sloppy molecular beacons and dual melting-temperature codes in a real-time PCR assay. Journal of Clinical Microbiology 49(3):932-940 (Mar. 2011).*
Piatek et al. Molecular beacon sequence analysis for detecting drug resistance in *Mycobacterium tuberculosis*. Nature Biotechnology 16:359-363 (1998).*
Ramirez et al, "Rapid detection of multidrug-resistant *Mycobacterium tuberculosis* by use of real-time PCR and high-resolution melt analysis," Journal of Clinical Microbiology (Sep. 1, 2010): 48(11):4003-4009.
El-Hajj et al., "Use of sloppy molecular becon probes for identification of mycobacterial specieis," Journal of Clincial Microbiology (Apr. 2009): 47(4):1190-1198.
Chakravorty et la., "Rapid, high-throughput detection of rifampin resistance and heteroresistance in *Mycobacterium tuberculosis* by use of sloppy molecular beacon metling temperature coding," Journal of Clincial Microbiology (Apr. 25, 2012): 50(7):2194-2202.

* cited by examiner

*Primary Examiner* — Samuel Woolwine
(74) *Attorney, Agent, or Firm* — Fox Rothschild LLP

(57) ABSTRACT

This invention relates to nucleic acids, reagents and methods for detecting Rifampicin-resistant *Mycobacterium tuberculosis* in a sample from a subject. In one aspect, the invention provides methods of detecting Rifampicin resistant *M. tuberculosis* in a sample comprising (a) amplifying a nucleic acid containing the rifampicin resistance determining region (RRDR) of the rpoB gene in a sample to provide an amplified nucleic acid; (b) probing the amplified nucleic acid with at least three molecular beacon probes for an RRDR mutant target; (c) conducting melting temperature (Tm) analysis to determine a Tm value for each probe; and (d) comparing the Tm value for each probe with a Tm value for a wild-type RRDR region, wherein a Tm value for at least one of the molecular beacon probes that is greater than the Tm value for the wildtype RRDR indicates the presence of rifampicin resistant *M. tuberculosis* in the sample.

14 Claims, 1 Drawing Sheet rpo1
(SEQ ID NO: 1)

rpo2
(SEQ ID NO: 2)

rpo3
(SEQ ID NO: 3)

SEQUENCE LISTING

```
<160> NUMBER OF SEQ ID NOS: 9

<210> SEQ ID NO 1
<211> LENGTH: 40
<212> TYPE: DNA
<213> ORGANISM: Artificial
<220> FEATURE:
<223> OTHER INFORMATION: Synthetic probe

<400> SEQUENCE: 1
cgaccgccca tgaattggct cagctggctg gtgacggtcg                           40

<210> SEQ ID NO 2
<211> LENGTH: 44
<212> TYPE: DNA
<213> ORGANISM: Artificial
<220> FEATURE:
<223> OTHER INFORMATION: Synthetic probe

<400> SEQUENCE: 2
ggcgcgaacc acgacagcgg gttgttctgg tccatgaacg cgcc                      44
```

```
<210> SEQ ID NO 3
<211> LENGTH: 44
<212> TYPE: DNA
<213> ORGANISM: Artificial
<220> FEATURE:
<223> OTHER INFORMATION: Synthetic probe

<400> SEQUENCE: 3
cgcgcgcatc accaacagtc ggtgcttgtg ggtcaacccg cgcg        44

<210> SEQ ID NO 4
<211> LENGTH: 43
<212> TYPE: DNA
<213> ORGANISM: Artificial
<220> FEATURE:
<223> OTHER INFORMATION: Synthetic probe

<400> SEQUENCE: 4
cgcggccgac agttggcgct tgtgggttaa ccccgacgcc gcg         43

<210> SEQ ID NO 5
<211> LENGTH: 41
<212> TYPE: DNA
<213> ORGANISM: Artificial
<220> FEATURE:
<223> OTHER INFORMATION: Synthetic probe

<400> SEQUENCE: 5
cgcgcgccgg gccccagcac caacagtcgg agcttcgcgc g           41

<210> SEQ ID NO 6
<211> LENGTH: 45
<212> TYPE: DNA
<213> ORGANISM: Artificial
<220> FEATURE:
<223> OTHER INFORMATION: Synthetic probe

<400> SEQUENCE: 6
cgcggcacga cagtttgcgc ttgtgggtca accccgactg ccgcg       45

<210> SEQ ID NO 7
<211> LENGTH: 19
<212> TYPE: DNA
<213> ORGANISM: Artificial
<220> FEATURE:
<223> OTHER INFORMATION: Synthetic probe

<400> SEQUENCE: 7
agacgttgat caacatccg                                    19

<210> SEQ ID NO 8
<211> LENGTH: 24
<212> TYPE: DNA
<213> ORGANISM: Artificial
<220> FEATURE:
<223> OTHER INFORMATION: Synthetic probe

<400> SEQUENCE: 8
acctccagcc cggcacgctc acgt                              24

<210> SEQ ID NO 9
<211> LENGTH: 20
<212> TYPE: DNA
<213> ORGANISM: Artificial
<220> FEATURE:
<223> OTHER INFORMATION: Synthetic probe
```

```
<400> SEQUENCE: 9
acatccggcc ggtggtcgcc                                                  20
```

DETECTION OF DRUG RESISTANT *MYCOBACTERIUM TUBERCULOSIS*

CROSS REFERENCE TO RELATED APPLICATION

This application is a U.S. National Phase of International Application No. PCT/US2013/035985, filed on Apr. 10, 2013, which claims the benefit of U.S. Provisional Application No. 61/622,403 filed Apr. 10, 2012, the disclosures of which are incorporated herein by reference in their entirety.

GOVERNMENT INTERESTS

The invention disclosed herein was made, at least in part, with Government support under Grant Nos. NIH AI 80653 and NIH AI 82174 from the National Institutes of Health. Accordingly, the U.S. Government has certain rights in this invention.

FIELD OF THE INVENTION

This invention relates to nucleic acids, reagents and methods for detecting Rifampicin-resistant *Mycobacterium tuberculosis* in a sample from a subject.

BACKGROUND OF THE INVENTION

Multi drug-resistant (MDR) and extensively drug resistant (XDR) *Mycobacterium tuberculosis* (TB) is increasing worldwide. *M. tuberculosis* does not naturally contain plasmids and almost all cases of clinical drug-resistance are caused by single-nucleotide polymorphisms (SNPs) or small insertions/deletions in relevant genes. In the case of Rifampicin-resistance, 95-98% of Rifampicin-resistant clinical strains have mutations in the eighty base pair Rifampicin Resistance Determining Region (RRDR) of the *M. tuberculosis* RNA polymerase beta (rpoB) gene. PCR and probe-based molecular genotyping assays can be used to detect these resistance-inducing mutations. Such genotypic assays are potentially more rapid than labor intensive culture-based drug susceptibility tests.

The Xpert MTB/RIF assay (Cepheid, Sunnyvale, Calif.) is one example of a genotypic test that is being increasingly used to screen for Rifampicin-resistance. However, the single use cartridge design of the Xpert assay limits its use for laboratory-based high-throughput testing. Several widely used reverse blot hybridization assays such as the INNO-LIPA Rif.TB assay (Innogenetics, Belgium) and the MTBDRplus (Hain, Germany) assay are available for laboratory-based Rifampicin-resistance screening; however, these assays are complicated by their open hybridization format. Open hybridization systems require a relatively cumbersome work process including rigorous physical separation of different work areas due to the risk of handling open PCR amplicons in a molecular diagnostic laboratory (Albert, H., et. al. 2010. BMC Infect Dis 10:41). Open systems also require a relatively large number of probes to test for relevant resistance-associated mutations. This requirement complicates assay chemistry and hybridization parameters. There is a need for a rapid single-PCR assay to identify Rifampicin-resistant *M. tuberculosis* with RRDR mutations, that has high sensitivity and specificity.

SUMMARY OF THE INVENTION

The invention generally relates to molecular beacon probes, and methods of using the molecular beacon probes to detect Rifampicin-resistant *M. tuberculosis*. This invention fulfills the need for a rapid single-PCR assay to identify Rifampicin-resistant *M. tuberculosis* with RRDR mutations, that has high sensitivity and specificity.

In one aspect, the invention provides methods of detecting Rifampicin resistant *M. tuberculosis* in a sample comprising (a) amplifying a nucleic acid containing the rifampicin resistance determining region (RRDR) of the rpoB gene in a sample to provide an amplified nucleic acid; (b) probing the amplified nucleic acid with at least three molecular beacon probes for an RRDR mutant target; (c) conducting melting temperature (Tm) analysis to determine a Tm value for each probe; and (d) comparing the Tm value for each probe with a Tm value for a wild-type RRDR region, wherein a Tm value for at least one of the molecular beacon probes that is greater than the Tm value for the wild-type RRDR indicates the presence of rifampicin resistant *M. tuberculosis* in the sample. The molecular beacon probe used may be a nucleic acid which is at least 85% identical to a nucleic acid having the sequence of SEQ ID NO:1, SEQ ID NO:2, SEQ ID NO:3, SEQ ID NO:4, SEQ ID NO:5, or SEQ ID NO:6. The sample may be a biological sample. The biological sample may be isolated from a subject.

In a second aspect, the invention provides a molecular beacon probe comprising a sequence which is at least 85% identical to SEQ ID NO:1, SEQ ID NO:2, SEQ ID NO:3, SEQ ID NO:4, SEQ ID NO:5, or SEQ ID NO:6, or the complement thereof. Preferably the molecular beacon probe comprises the nucleic acid sequence of SEQ ID NO:1, SEQ ID NO:2, SEQ ID NO:3, SEQ ID NO:4, SEQ ID NO:5, or SEQ ID NO:6.

In a third aspect, the invention provides a recombinant vector comprising an isolated nucleic acid comprising a sequence which is at least 85% identical, or at 100% identical to SEQ ID SEQ ID NO:1, SEQ ID NO:2, SEQ ID NO:3, SEQ ID NO:4, SEQ ID NO:5, or SEQ ID NO:6 or the complement thereof. The recombinant vector may be an expression vector. The invention further provides a host cell comprising the recombinant vector.

In a fourth aspect, the invention provides a host cell comprising a recombinant vector comprising an isolated nucleic acid comprising a sequence which is at least 85% identical, or 100% identical to SEQ ID SEQ ID NO:1, SEQ ID NO:2, SEQ ID NO:3, SEQ ID NO:4, SEQ ID NO:5, or SEQ ID NO:6, or the complement thereof.

In a fifth aspect, the invention provides a kit for detecting rifampicin resistant *M. tuberculosis* in a sample comprising at least one molecular beacon probe comprising a sequence which is at least 85% identical, or 100% identical to SEQ ID SEQ ID NO:1, SEQ ID NO:2, SEQ ID NO:3, SEQ ID NO:4, SEQ ID NO:5 or SEQ ID NO:6 or the complement thereof, and optionally further comprising nucleic acid primers for the amplification of the RRDR of the rpoB gene. The kit may further comprise reagents in a single container or separate containers, and instructions for use performing nucleic acid hybridization. The kit may contain reagents for PCR.

DETAILED DESCRIPTION OF THE INVENTION

Figure 1A:
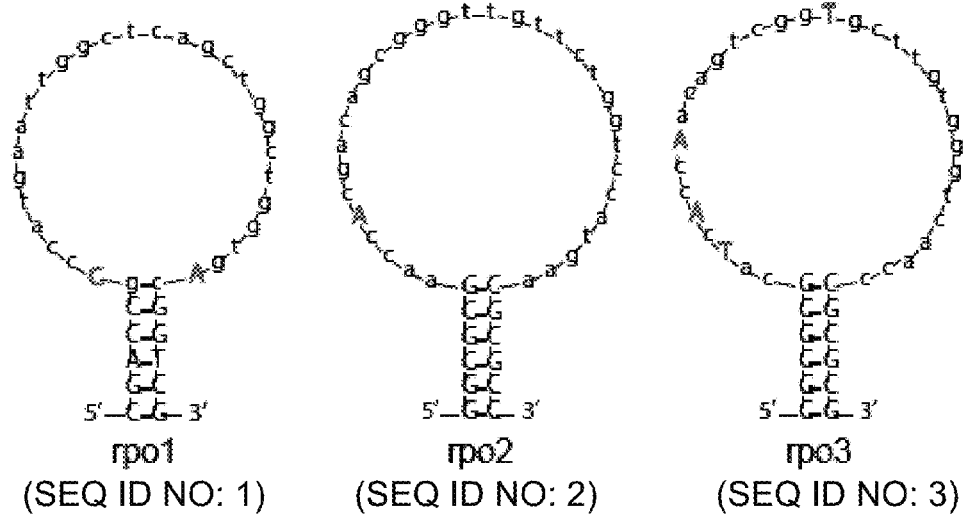
FIG. 1. depicts probes structures and Tm profiles against artificial targets. (A) The stable stem-loop structures of the three SMB probes used in the assay are shown. Related and unrelated mutations in the loop region introduced to obtain a stable stem-loop structure are shown in blue uppercase letters. Uppercase letters in black shows the stem regions. (B) Three probe Tm code of the assay tested against artificial targets with wild type or known RRDR mutations. Each horizontal line containing a square, circle and triangle represents a unique 3-point Tm code corresponding to a single RRDR sequence. Line 1 shows results for a wild type RRDR target, lines 2 to 45 show results for mutant RRDR targets. Mutants are detectable by the presence of a substantial shift in the Tm value of either one or more of the three Tm points. Lines 2-12 show RRDR sequences harboring mutations in the codons 507 to 514; Lines 13-24, RRDR sequences harboring mutations in the codons 515 to 522; Lines 25-35, RRDR sequences harboring mutations in the codons 526 to 529; Lines 36-43, RRDR sequences harboring mutations in the codons 531 to 533; Line 44 and 45 shows two RRDR double mutants.

This invention relates to nucleic acids, reagents and methods for detecting Rifampicin-resistant *Mycobacterium tuberculosis* in a sample. The mismatch-tolerant sloppy molecular beacon probes disclosed herein offer several advantages over the current generation of probe-based drug susceptibility tests. Unlike open hybridization assays, the methods disclosed herein are performed in a closed system, which greatly simplifies sample testing and minimizes cross contamination. Unlike high resolution Tm analysis detection methods, which detect mutations by recognizing subtle "melt curve variants" the methods disclosed herein produces clear and consistent Tm "peaks", which enables highly reproducible Tm value identification.

DEFINITIONS

"Biological sample" as used herein means a sample of biological tissue or fluid that comprises nucleic acids. Such samples include, but are not limited to, tissue isolated from animals. Biological samples may also include sections of tissues such as biopsy and autopsy samples, frozen sections taken for histologic purposes, blood, plasma, serum, sputum, saliva, stool, tears, mucus, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose).

"Complement" or "complementary" as used herein means Watson-Crick or Hoogsteen base pairing between nucleotides or nucleotide analogs of nucleic acid molecules.

As used herein, the terms "polynucleotide", "nucleotide sequence" or "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA. Examples of a nucleic acid include and are not limited to mRNA, miRNA, tRNA, rRNA, snRNA, siRNA, dsRNA, cDNA and DNA/RNA hybrids. Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid may be used for the same purpose as a given nucleic acid. Thus, a nucleic acid also encompasses substantially identical nucleic acids and complements thereof. As will also be appreciated by those in the art, a single strand provides a probe for a probe that may hybridize to the target sequence under stringent hybridization conditions. Thus, a nucleic acid also encompasses a probe that hybridizes under stringent hybridization conditions.

The term "in operable combination", "in operable order" or "operably linked" refers to the linkage of nucleic acid sequences in such a manner that a nucleic acid molecule capable of directing the transcription of a given gene and/or the synthesis of a desired protein molecule is produced.

"Rifampicin" may be used interchangeably with "Rifampin", and refers to rifamycin, the family of antibiotics originally isolated from a strain of the soil microorganism *Streptomyces mediterranei*, used in the treatment of leprosy, tuberculosis, and other bacterial diseases.

"Molecular beacon probe" as used herein refers to a hybridization probe that forms a stem and loop structure. The molecular beacon probe may range in length from 5 nucleotides to a 1000 nucleotides, most preferably from 10 to 50 nucleotides in length The molecular beacon probe has a 5' arm, a loop portion that is a probe sequence, and a 3' arm. The 5' and 3' arms are complementary to each other but not to the loop portion or the target, and bind to each other to form the stem of the molecular beacon probe. The arms are preferably from 3-10 nucleotides in length, and more preferably from 5-7 nucleotides in length. Probes may bind target sequences lacking complete complementarity with the probe sequence depending upon the stringency of the hybridization conditions. The molecular beacon probes of the present invention are mismatch tolerant and may contain a substantial number of mismatched base pairs relative to the target, and thus are also referred to herein as "sloppy molecular beacons" or "SMBs". In a preferred embodiment, a fluorophore is attached to one end of the molecular beacon probe and a non-fluorescent quencher moiety is attached to the other end. For example, the molecular beacon probe may have a fluorophore attached to the 5'-end and a quencher moiety attached to the 3'-end, or a fluorophore attached to the 3'-end and a quencher moiety attached to the 5'-end. Fluorophores are known in the art and include fluorescein, rhodamine and cyanine derivatives. Quenchers are known in the art and include Black Hole Quenchers (Biosearch Technologies, Novato, Calif.).

"Stringent hybridization conditions" as used herein refers to conditions under which a first nucleic acid sequence (e.g., probe) will hybridize to a second nucleic acid sequence (e.g., target), such as in a complex mixture of nucleic acids, but to no other sequences. Stringent conditions are sequence-dependent and will be different in different circumstances. One with ordinary skill can determine the appropriate conditions according to standard assays known in the art.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

"Substantially complementary" as used herein refers to that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50 or more nucleotides, or that the two sequences hybridize under stringent hybridization conditions.

"Substantially identical" as used herein refers to that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50 or more nucleotides or amino acids, or with respect to nucleic acids, if the first sequence is substantially complementary to the complement of the second sequence.

"Target" as used herein means a polynucleotide that may be bound by one or more probes under stringent hybridization conditions.

"Promoter" as used herein refers to a synthetic or naturally-derived molecule which is capable of conferring or activating expression of a nucleic acid in a cell. A promoter may comprise one or more specific regulatory elements to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Vector" as used herein refers to a nucleic acid sequence containing an origin of replication. A vector may be a plasmid, bacteriophage, bacterial artificial chromosome, yeast artificial chromosome or a virus. A vector may be a DNA or RNA vector. A vector may be either a self-replicating extrachromosomal vector or a vector which integrates into a host genome. The term "expression vector" refers to a nucleic acid assembly containing a promoter which is capable of directing the expression of a sequence or gene of interest in a cell. Vectors typically contain nucleic acid sequences encoding selectable markers for selection of cells that have been transfected by the vector. Generally, "vector construct," "expression vector," and "gene transfer vector," refer to any nucleic acid construct capable of directing the expression of a gene of interest and which can transfer gene sequences to target cells or host cells.

Methods for Detecting Rifampicin Resistant *M. tuberculosis* in a Sample

In one embodiment, this invention provides methods to detect Rifampicin resistant *M. tuberculosis* in a sample. Rifampicin-resistance in *M. tuberculosis* is largely determined by mutations in an eighty base pair Rifampicin Resistance Determining Region (RRDR) of the rpoB gene. The methods described herein use sloppy molecular beacons as probes to detect such mutations. The invention provides methods of detecting Rifampicin resistant *M. tuberculosis* in a sample comprising (a) amplifying a nucleic acid containing the rifampicin resistance determining region (RRDR) of the rpoB gene in a sample to provide an amplified nucleic acid; (b) probing the amplified nucleic acid with at least three molecular beacon probes for an RRDR mutant target; (c) conducting melting temperature (Tm) analysis to determine a Tm value for each probe; and (d) comparing the Tm value for each probe with a Tm value for a wild-type RRDR region, wherein a Tm value for at least one of the molecular beacon probes that is greater than the Tm value for the wild-type RRDR indicates the presence of rifampicin resistant *M. tuberculosis* in the sample. The molecular beacon probe used may be a nucleic acid which is at least 85% identical, or 100% identical, to a nucleic acid having the sequence of SEQ ID NO:1, SEQ ID NO:2, SEQ ID NO:3, SEQ ID NO:4, SEQ ID NO:5, or SEQ ID NO:6. The sample may be a biological sample. The biological sample may be isolated from a subject.

Nucleic acids containing the RRDR region may be amplified by methods known in the art, e.g., by standard PCR (U.S. Pat. No. 4,683,202), RT-PCR (Bustin S. J Mol Endocrinol. 25:169-93, 2000), quantitative PCR (Ong Y. et al., Hematology. 7:59-67, 2002), real time PCR (Ginzinger D. Exp Hematol. 30:503-12, 2002), in situ PCR (Thaker V. Methods Mol Biol. 115:379-402, 1999), and symmetric and asymmetric PCR (Poddar (2000) Molecular and Cellular Probes 14:25-32). In a preferred embodiment, amplification is by asymmetric PCR.

One of skill in the art can determine suitable primers useful for amplification.

Melting temperature (Tm) analysis may be performed by methods known in the art and disclosed for example by Chakravorty et al. (2011) Journal of Clinical Microbiology 49:932-940. A three-point Tm code can be generated to distinguish wild-type from mutant RRDR DNA sequences in approximately two hours.

A sample may contain both wild-type and mutant RRDR. Preferably, a control sample is a wild-type RRDR DNA sequence without any mutations A sample containing nucleic acids that encode the RRDR region can be detected using at least one probe that is substantially identical to SEQ ID NO:1, SEQ ID NO:2, SEQ ID NO:3, SEQ ID NO:4, SEQ ID NO:5, or SEQ ID NO:6. The probe may also be at least 85% identical to SEQ ID NO:1, SEQ ID NO:2, SEQ ID NO:3, SEQ ID NO:4, SEQ ID NO:5, or SEQ ID NO:6. Samples suspected of containing *M. tuberculosis* can be isolated from biological samples using any of a number of well-known procedures The mismatch-tolerant SMB probes, SEQ ID NOs. 1, 2, 3, 4, 5, and 6, that are used offer several advantages over the current generation of probe-based drug susceptibility tests. Unlike open hybridization assays, the methods are performed in a closed system, which greatly simplifies sample testing and minimizes cross contamination. Unlike high resolution Tm analysis (HRMA) detection methods, which detect mutations by recognizing subtle "melt curve variants" the disclosed method produces clear and consistent Tm "peaks", which enables highly reproducible Tm value identification.

The SMB probes allow versatility in sequence recognition while maintaining a robust capacity to discriminate mutations. The three-point Tm code created using the methods disclosed herein can either specifically identify RRDR mutations or group them into easily identifiable mutation clusters. The methods do not depend on high resolution Tm capabilities. Unlike other assays which focus mainly on identifying the most common clinically prevalent mutations, the methods disclosed herein can be used to detect both the common as well as uncommon mutations over the entire RRDR sequence. The large probe regions permitted by the SMB probes make it possible to use just three probes to target the entire 80 bp rpoB RRDR sequence. The methods disclosed herein allow for the identification of every type of mutation tested including nucleotide transitions, transversions, deletions and insertions along with several double mutations.

The present invention further provides an isolated nucleic acid comprising a nucleotide sequence of SEQ ID NO:1, SEQ ID NO:2, SEQ ID NO:3, SEQ ID NO:4, SEQ ID NO:5, or SEQ ID NO:6 and variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 1500 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80 or 90 nucleotides. The nucleic acid may be chemically synthesized or expressed in a cell (in vitro or in vivo) using a vector described below. The nucleic acid may be synthesized as a single strand molecule and hybridized under stringent hybridization conditions to a substantially complementary nucleic acid to form a duplex, which is considered a nucleic acid of the invention. The nucleic acid may be introduced to a cell, tissue or organ in a single- or double-stranded form or capable of being expressed by a vector using methods well known to those skilled in the art. MOLECULAR CLONING A LABORATORY MANUAL (3rd Ed., ed. by Sambrook, Fritsch and Maniatis (Cold Spring Harbor Laboratory Press: 2001) describes commonly used techniques in molecular biology.

In particular variants of the nucleic acid, for example deletions, insertions, and/or substitutions in the sequence, which cause for so-called "silent changes", are considered to be part of the invention.

According to the present invention nucleic acids can show for example at least about 70%, more typically at least about 85%, 90% or 95% sequence identity to the nucleic acid sequences of SEQ ID NO:1, SEQ ID NO:2, SEQ ID NO:3, SEQ ID NO:4, SEQ ID NO:5, SEQ ID NO:6.

The present invention provides a vector comprising a nucleic acid comprising a sequence which is at least 85% identical to SEQ ID NO:1, SEQ ID NO:2, SEQ ID NO:3, SEQ ID NO:4, SEQ ID NO:5, or SEQ ID NO:6. The present invention also provides a vector comprising a nucleic acid which hybridizes to the nucleic acid of SEQ ID NO:1, SEQ ID NO:2, SEQ ID NO:3, SEQ ID NO:4, SEQ ID NO:5, or SEQ ID NO:6 under high stringency conditions. An expression vector may comprise additional elements. For example, the expression vector may have two replication systems allowing it to be maintained in two organisms, e.g., in mammalian or insect cells for expression and in a prokaryotic host for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker to allow the selection of transformed host cells.

The present invention provides a host cell comprising a vector of the invention. The cell may be a bacterial, fungal, plant, insect or animal cell. Methods are known in the art to introduce the nucleic acids of the present invention to a host cell, including electroporation and standard methods of transfection. MOLECULAR CLONING A LABORATORY MANUAL (3rd Ed., ed. by Sambrook, Fritsch and Maniatis (Cold Spring Harbor Laboratory Press: 2001) describes commonly used techniques in molecular biology.

The present invention provides a kit for detection of rifampicin resistant *M. tuberculosis* comprising one or more molecular beacon probes and optionally a pair of primers for amplification of the RRDR of the rpoB gene. Preferably, the kit includes one or more probes that are at least 85% identical, or 100% identical, to SEQ ID NO:1, SEQ ID NO:2, SEQ ID NO:3, SEQ ID NO:4, SEQ ID NO:5, or SEQ ID NO:6. The probes may optionally have a fluorophore attached to one end and a non-fluorescent quencher moiety attached to the other end.

The kit may be comprised of one or more containers and may also include collection equipment, for example, bottles, bags (such as intravenous fluids bags), vials, syringes, and test tubes. Other components may include needles, diluents and buffers. The kit may comprise reagents for PCR and may further comprise instructions for performing the method of detection of rifampicin resistant *M. tuberculosis* disclosed herein.

In addition, one or more materials and/or reagents required for preparing a biological sample for the isolation of the RRDR are optionally included in the kit. Furthermore, optionally included in the kits are one or more enzymes suitable for amplifying nucleic acids, including various polymerases (RT, Taq, etc.), one or more deoxynucleotides, and buffers to provide the necessary reaction mixture for amplification.

Optionally, the kits of the invention further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

EXAMPLES

The invention now being generally described, it will be more readily understood by reference to the following examples, which are included merely for purposes of illustration of certain aspects and embodiments of the present invention, and are not intended to limit the invention.

Materials and Methods

Clinical DNA Samples:

Clinical samples from two sample sets were tested in order to include a wide variety of mutations and geographic origins. The first sample set consisted of 440 sequential *M. tuberculosis* isolates cultured from patients enrolled in a natural history study of MDR-TB (NCT00341601 at clinicaltrials.gov) in the National Masan Tuberculosis Hospital in Changwon, Republic of Korea for which reliable conventional drug-susceptibility tests and/or DNA sequencing of the *M. tuberculosis* RRDR region were available. The second sample set consisted of 149 selected *M. tuberculosis* cultures obtained from the WHO TDR Tuberculosis Specimen Bank maintained by the United Nations Children's Fund/UNDP/World Bank/WHO Special Program for Research and Training in Tropical Diseases, which includes cultures from Africa, Asia, Australia, Europe and Latin America, for a total of 589 DNA samples tested. The TDR samples were chosen to represent a wide repertoire of RRDR mutants and a broad geographical distribution for both RRDR mutants and Rifampicin-susceptible controls. Conventional Rifampicin susceptibility was performed using the LJ proportions method with 40 μg/ml used as the critical Rifampicin-concentration defining Rifampicin-resistance (Van Deun, et. al. 2009. J Clin Microbiol 47:3501-3506). Rifampicin-resistance results were available for 561 out of the 589 samples. The RRDR sequence, and in most cases the entire rpoB gene sequence was available for all 589 isolates. A subset of RRDR mutants were resequenced, representing all of the different mutations tested in the study, to confirm the original DNA sequence results. The results of the DNA sequencing performed as part of this current study were used in the rare event of discordance with the prior sequencing result. Each DNA sample was quantified with a Nanodrop microvolume spectrophotometer (Thermo Scientific, USA), and 2 to 5 ng of the DNA sample was used for PCR. All samples were independently coded and randomly redistributed to blind the sample sequence and origin before performing each test assay.

DNA Samples from Human Origin, Nontuberculous Mycobacteria (NTM), and Gram-Positive and Gram-Negative Bacteria.

Pure human genomic DNA obtained from the ATCC repository (Manassas, Va., USA), a sample of 121 clinical NTM cultures isolated from patients at the National Masan Tuberculosis Hospital representing 26 species, 18 NTM isolates obtained from the ATCC repository (Manassas, Va., USA) consisting of *M. abscessus, M. scrofulaceum, M. celatum, M. haemophilum, M. asiaticum, M. kansasii, M. avium, M. flavescens, M. szulgai, M. terrae, M. fortuitum, M. intracellulare, M. marinum, M. xenopi, M. thermoresistible, M. simiae, M. trivial* and *M. malmoense*, and DNA extracted from 18 species of Gram-negative and Gram-positive bacteria representing the most common bloodstream infections and nosocomial pathogens obtained from various sources were selected to test for the analytical specificity. DNA was isolated from pure clinical strains by boiling a loopful of culture in Instagene matrix solution (Bio-Rad, USA). The DNA was quantified as described above, and tested using 100 to 400 ng for each PCR. To test for the capability of the assay to detect *M. tuberculosis* RRDR mutations in presence of a 10 fold excess of background NTM DNA, $10^5$ genome equivalents of *M. tuberculosis* DNA harboring common RRDR mutations found in our study (516GTC, 526TAC, 531TTG and 533CCG) was mixed with $10^6$ genome equivalents of NTM DNA. Human DNA was tested in $10^5$ fold excess compared to the target *M. tuberculosis* DNA.

Sloppy Molecular Beacons Probes (SMBs) and Primers.

A 172 bp fragment (nucleotides 1226-1397, numbering based on the gene start site according to the *Escherichia coli* DNA nomenclature) containing the rpoB RRDR region was amplified using the target (forward) primer rpoB-F 5'-agacgttgatcaacatccg-3'(SEQ ID NO. 7) and the antisense (reverse) primer rpoB-R 5'-acctccagcccggcacgctcacgt-3' (SEQ ID NO. 8). The following primer, 5'-acatccggccggtg-gtcgcc-3' (SEQ ID NO. 9:) may also be used as a forward primer. These primers were designed to be specific to the *M. tuberculosis* complex, verified by an alignment of *M. tuberculosis* and all the NTM rpoB sequences available in the genbank database (http://www.ncbi.nlm.nih.gov/genbank/). Three SMB probes: rpo1 (5'-tetramethylrhodamine-cgaccgCccatgaattggctcagctggctggtgAc ggtcg-BHQ2-3')(SEQ ID NO. 1), rpo2 (5'-cyanine 5-ggcgcgaaccAcgacagcgggttgttctggtccatagaa cgcgcc-BHQ2-3')(SEQ ID NO. 2) and rpo3 (5'-6 carboxy-fluorescein-cgcgcgcaTcAccAacagtcggTgcttgtgggtcaacc cgcgcg-BHQ1-3')(SEQ ID NO. 3) where the underlined bold sequences represent the stem portion of the SMB, the lowercase sequences represent the probe portion of the SMB, uppercase letters represent the mutations introduced into the probe region to obtain a stable stem-loop structure and BHQ represents Black Hole Quencher, were targeted against the rpoB RRDR region. The SMBs were designed using the in-silico DNA folding program http://frontend.bio-info.rpi.edu/applications/mfold/cgi-bin/dna-form1.cgi and the probe-target hybrid folding program http://dinamelt.bio-info.rpi.edu/twostate.php was used to predict the possible probe-target hybrid structures and Tms. The probes were designed to generate a maximum Tm difference between wild type and mutant sequences in their respective target regions of the RRDR, so as to enable their unambiguous identification. Primers were obtained from Sigma Genosys, USA and the SMB probes from Biosearch, Calif., USA.

Other SMB probes that may be used include:

```
TS-rpo3:
                                        (SEQ ID NO. 4)
CGCGGCcgacagtTggcgcttgtgggtTaaccccgacGCCGCG TS-rpo4:
                                        (SEQ ID NO. 5)
CGCGCGccgggccccagcAccAacagtcggAgcttCGCGCG U-rpo3a-TT:
                                        (SEQ ID NO. 6)
CGCGGCAcgacagtTTgcgcttgtgggtcaaccccgacTGCCGCG
```

Using Artificial Oligonucleotides Containing rpoB RRDR Mutations to Test Assay Probes.

To test the assay against the broadest range of RRDR mutations, oligonucleotides containing either wild type or mutant RRDR sequence were created, including 44 clinically relevant mutations identified as being present in at least 0.1% frequency in clinical settings (based on an extensive literature search) to test the ability of the assay probes to identify different RRDR sequence types. The 44 different mutations spanning the RRDR from codons 507 to 533 included SNPs, insertions, and double mutants (Table 1). The Tm of each of the three SMB probes in the presence of each RRDR oligonucleotide target was measured. Approximately 500 ng of individual oligonucleotide targets were added to a reaction mixture containing 0.8 ng/μl of each SMB probe, 4 mM $MgCl_2$, 1×PCR buffer (10× Stoffel Buffer, Applied Biosystems, USA) and 5% glycerol. Tm analysis was performed using a Light Cycler 480 II real time PCR system (Roche Molecular Systems Inc., USA) using the following assay parameters; denaturation at 95° C. for 5 min followed by cooling down to 45° C. and then gradual heating to 85° C. with continuous monitoring of the fluorescence during the process at a rate of 10 data acquisitions per degree centigrade. Tm calls were performed at the end of the reaction using the automated Tm calling software (Light Cycler 480 software) and resulting Tm values for each probe were determined. The three Tm values (one for each SMB probe) that were generated in the presence of an RRDR target where then used to define a three-point Tm "code" for each RRDR mutant or wild type sequence.

Sloppy Molecular Beacon Tm Assay on Clinical DNA.

Each DNA sample was quantified using a Nanodrop microvolume spectrophotometer (Thermo Scientific, USA), and 2 to 5 ng of the DNA sample was used for each PCR, except where indicated. PCR was performed in 384 well plates using the Roche Light Cycler 480 II real time PCR system (Roche Molecular Systems Inc., USA), in 20 μl reaction volumes containing 1 μM of target primer and 50 nM of the antisense primer, 0.8 ng/μl of each SMB probe, 4 mM MgCl$_2$, 250 mM dNTPs, 1×PCR buffer, 5% glycerol, 0.06 U/μl of Amplitaq Gold Stoffel DNA Polymerase (Applied Biosystems, USA), and 2-5 ng of sample DNA or an equivalent volume of water. PCR was carried out as follows: Activation of the enzyme for 2 minutes at 95° C., followed by 45 cycles of denaturation at 95° C. for 15 seconds, annealing at 65° C. for 30 seconds and extension at 72° C. for 10 seconds. Following PCR cycling, post PCR Tm analysis was performed by denaturation at 95° C. for 5 min followed by cooling down to 45° C. and then gradual heating to 85° C. with continuous monitoring of the fluorescence during the process at a rate of 10 data acquisitions per degree centigrade. Tm calls were performed at the end of the reaction using the automated Tm calling software (Light Cycler 480 software) and resulting Tm values for each probe were determined. A non-template control using sterile water instead of DNA as template was used as "DNA negative control" and a DNA positive control using 1 ng of genomic DNA from M. tuberculosis H37Rv as template was also included in each assay plate.

Assay Limit of Detection.

The analytical sensitivity of the assay was determined using serial dilutions of three different genomic DNA samples. One sample had a wild type RRDR sequence and one sample each had the RRDR mutations 516GTC and 531TTG, which were chosen because these two mutations occurred frequently in our clinical DNA panel and in the literature. Each DNA sample was serially diluted to represent a concentration range from $10^6$ through 10 genome equivalents per reaction. The rpoB SMB assay was performed ten times at each dilution, and the minimum DNA concentration which produced correct Tm codes 100% of the time was determined as the limit of detection (LOD) of the assay for that RRDR type.

DNA Mixtures Containing Wild Type and 531TTG Mutant DNA.

DNA mixtures containing wild type and mutant DNA were prepared to evaluate the performance of the assay in mixed samples containing both wild type and RRDR mutant DNA (heteroresistance). This situation might occur clinically in a dual M. tuberculosis infection or during in vivo evolution of Rifampicin resistance caused by tuberculosis treatment. Various amounts of the 531TTG mutant genomic DNA (a representative highly prevalent RRDR mutation) was added to wild type M. tuberculosis DNA to generate DNA mixtures containing 10 through 90% mutant DNA in ten percent increments in a total DNA amount of 10 ng ($10^6$ genome equivalents). SMB Tm shift assays and Sanger sequencing of the RRDR were performed on each mixed DNA type to compare the ability of the SMB assay to detect the RRDR mutant in this mixture to that of Sanger DNA sequencing.

Sanger DNA Sequencing:

DNA samples were amplified using rpoB gene specific primers as described above except for the fact that 0.5 μM of both forward and reverse primers, 2.5 mM MgCl$_2$ and 0.03 U/μl of AmpliTaq Gold DNA polymerase (Applied Biosystems) were used. The amplified products were checked by gel electrophoresis and then purified using a PCR purification kit (Qiagen) following the manufacturer's instructions. The purified PCR products were subjected to bi-directional sequencing using both the rpoB gene specific forward and reverse primers in a 3130XL Genetic Analyzer (Applied Bio-systems) using BigDye Terminator Version 3.1 Cycle sequencing kit (Applied Biosystems) according to manufacturer's instructions.

Results

SMB Design Parameters Produce a Gradient of Tm Values which Differentiate Mutant from Wild Type RRDR Sequences.

To identify Rifampicin-resistance associated mutations in the M. tuberculosis RRDR, three SMB probes were designed, "rpo1 (SEQ. ID NO. 1)", "rpo2 (SEQ ID NO. 2)" and "rpo3 (SEQ ID NO. 3)", which contained 28 to 32-bp probe sequences and 5 to 6-bp stem sequences. The probes were designed to generate stable stem-loop structures while avoiding the formation of secondary structures in the loop region. The rpo1 probe targeted RRDR codons 507 to 516, rpo2 targeted codons 514 to 523 and rpo3 targeted codons 524 to 533. Each probe was designed to specifically detect all clinically relevant resistance-associated RRDR mutations spanning the codons targeted by the respective probes. A stable stem loop structure is necessary for optimal binding kinetics between the SMB probes and the M. tuberculosis DNA target, and for the production of distinct Tm values corresponding to each RRDR mutation. The stem-loop structures for all three probes were stabilized by introducing mutations into the probe loop to disrupt secondary structures and palindromes (FIG. 1A). The mutations introduced were chosen to either be complementary to a known RRDR mutation or to be unrelated to any known nucleotide at that position, depending on assay requirements and on the resulting probe structure. Among the Rifampicin-resistance associated mutations introduced, probe rpo1 included a 516GGC mutation instead of wild type sequence and rpo3 included 531TTG and 533ATG mutations instead of wild type sequence. The inclusion of RRDR resistance-associated mutations within the SMB probes produced a gradient of probe-target relatedness, with certain common RRDR mutations producing Tm values higher than wild type RRDR and other (less commonly-occurring) RRDR mutations producing Tm values lower than wild type RRDR (Table 1, FIG. 1B).

Figure 1B:
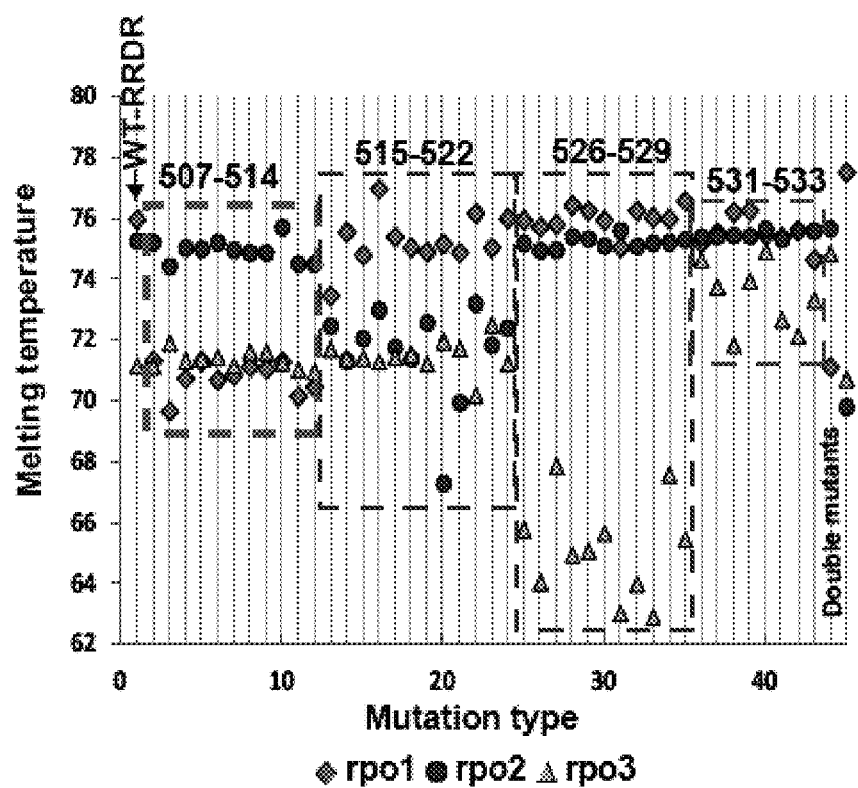

The Tm of all three SMBs was measured in the presence of wild type RRDR and each of the RRDR mutant targets using artificial oligonucleotides. A "three-point Tm" code for each oligonucleotide target was generated by this procedure (Table 1). The Tm code for wild type target could be distinguished from RRDR mutant targets in all cases. For 41 of the 44 RRDR mutants, at least one of the three SMBs had a Tm value difference (dTm) of at least 2.1° C. compared to the wild type RRDR (Table 1, FIG. 1B). Many dTms were even higher. Targets containing common double mutants also had at least one probe with a dTm of at least 2.1° C. (Table 1, FIG. 1B). Three less commonly-occurring RRDR mutations 531GCG, 531TAG and 533CCG were detected with dTms of −0.7, −1.5 and −1.0° C. respectively. However, these mutants produced larger dTms when chromosomal DNA from clinical M. tuberculosis isolates was tested. The RRDR mutants could also be conveniently grouped into "Tm code" clusters corresponding to the codons tested by the individual probes (FIG. 1B).

Assay Tm Profiles of Clinical Samples Compared to DNA Sequencing.

The ability of the SMB assay to detect RRDR mutations against a panel of 589 clinical samples of diverse geographical origin was evaluated (Table 2). The test panel included 236 RRDR mutant samples and 25 different RRDR mutation genotypes distributed over eleven codons, including the common clinical mutations, double mutants, codon insertions and deletions (Table 2). The predominant mutation type was 531TTG (62%) followed by 516GTC (8.8%), 526TAC (7%) and 533CCG (4%) with the other genotypes contained in the remaining 18% of the RRDR mutants. The assay identified 236/236 (sensitivity 100%, 95% CI 98.0%-100.0%) RRDR mutants correctly, including 234/234 samples that contained only mutant DNA, and 2/2 samples that were identified as heteroresistant mixed infections, by DNA sequencing. For 24 out of the 25 mutations, the average dTm values were between ±2.4 to 9.7° C. for at least one of the three probes (Table 2). The ten samples with a 533CCG mutation had dTms ranging from −1.0 to −1.5° C. Thus, the tests of clinical samples identified all RRDR mutants in contrast to tests of oligonucleotides where 3/44 RRDR mutations showed smaller dTms, making them more difficult to detect. Assay specificity was also high with 353/353 (100%, 95% CI 98.7%-100.0%) samples with wild type RRDR sequences being correctly identified as having wild type RRDR by the SMB assay. The 353 wild type samples had mean dTm values for rpo1, rpo2 and rpo3 of 69.7±0.18, 69.7±0.21, and 64.9±0.29° C. respectively (Table 2).

All of the wild type and mutant DNA samples generated an identifiable three Tm code which enabled grouping of the RRDR mutants into smaller clusters that contained one or more possible mutations as observed with the artificial targets (Table 2). Specifically, the assay clustered single mutants, insertions and deletions into the following groups, 511/513 mutant, 513-514CAA insertion, 516AAC/522TTG, 516GTC, 516CTC, 516TAC, 516GGC, 518AAC deletion, 526CGC, 526TGC/CTC/TAC, 526GAC, 531CAG/TTG, 531TGG and 533CCG (Table 2, FIG. 1B). Double mutants were identified by the presence of characteristic dTms from more than one probe (Table 2).

Comparison to Phenotypic Drug Susceptibility Testing.

The performance of the rpoB SMB assay was compared to phenotypic drug susceptibility testing in the 561 samples for which Rifampicin drug susceptibility testing results were available. Sensitivity for resistance was 222/225 (98.7%, 95% CI, 95.8%-99.6%) and specificity was 335/336, (99.7%, 95% CI, 98.1%-99.9%). Among the Rifampicin resistant false-negatives, three contained rpoB mutations outside of the RRDR (251TTC, 331CCC and 572TTC). The single Rifampicin resistant false positive occurred in a sample that was found to have an rpoB 511CCG mutation upon DNA sequencing. Clinical isolates with 511CCG mutations are prone to be misreported as Rifampicin-susceptible by phenotypic Rifampicin susceptibility assays. Thus, this particular clinical strain may have been truly Rifampicin-resistant. In fact, two other isolates in the study with 511CCG mutation were reported to be phenotypically Rifampicin-resistant. Cultures of this isolate were not available for repeat phenotypic susceptibility testing. The SMB assay and phenotypic drug susceptibility results were concordant for all of the other 557 samples tested.

Analytical Specificity of the Assay.

The analytical specificity of the assay was further tested using DNA extracted from 121 clinical and 18 reference NTM species and strains and 18 species of gram positive and gram negative bacteria. None of the NTMs except for *M. malmoense* generated a perceptible signal from any of the 3 probes. Very high concentrations of *M. malmoense* DNA (100 to 200 ng) caused the rpo2 probe to generate a Tm of 70° C., but no measurable Tm values were generated for the rpo1 and rpo3 probes. This triple Tm code (0, 70, 0) was quite distinct from all of the other Tm codes obtained on tests of both wild type and mutant RRDR *M. tuberculosis* DNA. None of the gram positive or gram negative bacteria tested produced a measurable signal. To test for possible interference from NTM DNA, $10^6$ genome equivalents of *M. malmoense, M. abscessus, M. avium, M. chelonae, M. gordonae, M. intracellulare* or *M. kansasii* DNA with $10^5$ genome equivalents of *M. tuberculosis* DNA containing RRDR mutations at 516GTC, 526TAC, 531TTG or 533CCG were mixed. Each RRDR mutant was correctly identified despite the presence of the excess NTM DNA (Table 3). Further increasing the *M. malmoense* DNA concentration to 20-50 fold excess compared to *M. tuberculosis* DNA caused the rpo2 probe to generate a double Tm peak in the presence of the *M. tuberculosis* 516GTC and 516AAC RRDR mutants (Table 3). When a double peak was visualized, one of the double peaks corresponded to the Tm expected for the *M. tuberculosis* RRDR mutant and the other peak corresponded to the Tm expected for *M. malmoense* DNA. *M. malmoense* DNA alone when used at 20 to 50 ng concentration generated a single peak with Tm of 70° C. corresponding to the rpo2 probe, which did not mimic the wild type or any of the RRDR mutant three probe Tm profile. These results indicate that NTM co-infections will not affect assay results in regards to *M. tuberculosis* Rifampicin-susceptibility. The assay was also found to be unaffected by the presence of as much as $10^5$ fold excess human genomic DNA as compared to *M. tuberculosis* DNA. The assays capacity for mutation detection also remained unaltered, indicating that human genomic DNA from sputum should not interfere with the assay's performance.

Assay Limit of Detection (LOD):

Genomic DNA from *M. tuberculosis* containing wild type rpoB RRDR and two most common RRDR mutations, 516GTC and 531TTG, were chosen to determine the limit of detection of the rpoB SMB assay. DNA samples were serially diluted from 10 ng to 100 fg per microliter in ten-fold decrements and the SMB assay was performed on 2 µl of each individual dilution 10 times. The Tm values obtained at different concentrations were independent of the initial amount of target DNA put into the reaction for *M. tuberculosis* with wild type RRDR and mutant RRDR, when Tm peaks could be measured. Each probe had a characteristic LOD below which no Tm value could be observed. The limit of detection (LOD) assay was defined as the DNA concentration below which at least one probe could not consistently measure a Tm (probe rpo3 in this case). For the wild type and the mutant DNA samples the assay could detect 20 and 2 pg of DNA correctly 100% of the time which is approximately 2,000 and 200 *M. tuberculosis* genome equivalents respectively. These results indicate that the assay should to detect Rifampicin resistance in DNA extracted from all smear-positive and many smear negative patient samples.

Detection of Mixed-Sequence Mutation, for Example, Detection of 531TTG Mutation in DNA Mixtures.

The ability of the rpoB SMB probe assay to detect the RRDR mutant in this mixture was compared to Sanger DNA sequencing. The SMB probe assay detected the presence of the RRDR mutation down to a concentration of 40% mutant DNA, as indicated by the double peak of Tm values. The mutant Tm peak became increasingly prominent as more mutant DNA was present in the mixture. DNA mixtures with 10, 20 and 30% mutant DNA showed a single wild type Tm peak and were indistinguishable from a sample containing 100% wild type DNA. Using the same DNA mixtures to perform bi-directional sequencing of the rpoB amplicon, the unequivocal presence of the mutant DNA was only apparent on sequencing chromatograms when at least 50% mutant DNA was present. Thus, the SMB probe assay detected mixed infections at least as well as Sanger DNA sequencing.

TABLE 1

Three probe Tm (° C.) code of the assay in tests of artificial oligonucleotide targets with wild type and mutant RRDR sequences[a]

| | Sample | Mutation | Tm rpo1 | Tm rpo2 | Tm rpo3 | dTm rpo1 | dTm rpo2 | dTm rpo3 |
|---|---|---|---|---|---|---|---|---|
| #1 | WT* | | 76.0 | 75.3 | 71.2 | | | |
| #2 | 507 | ggc-gac | 71.3 | 75.2 | 71.2 | 4.7 | 0.0 | 0.0 |
| #3 | 510 | cag-cac | 69.7 | 74.4 | 71.9 | 6.3 | 0.8 | -0.7 |
| #4 | 511 A | ctg-ccg | 70.7 | 75.0 | 71.3 | 5.2 | 0.2 | -0.1 |
| #5 | 511 B | ctg-cgg | 71.3 | 75.0 | 71.4 | 4.7 | 0.3 | -0.2 |
| #6 | 512 | agc-acc | 70.7 | 75.2 | 71.4 | 5.3 | 0.1 | -0.3 |
| #7 | 513 A | caa-aaa | 70.9 | 75.0 | 71.2 | 5.1 | 0.3 | 0.0 |
| #8 | 513 B | caa-cca | 71.1 | 74.9 | 71.6 | 4.9 | 0.4 | -0.4 |
| #9 | 513 C | caa-cta | 71.1 | 74.9 | 71.6 | 4.9 | 0.4 | -0.4 |
| #10 | 514 A | ttc insertion | 71.3 | 75.7 | 71.3 | 4.7 | -0.5 | -0.1 |
| #11 | 514 B | ttc-ttg | 70.2 | 74.5 | 71.0 | 5.8 | 0.8 | 0.1 |
| #12 | 514 C | ttc-ttt (silent) | 70.5 | 74.5 | 71.0 | 5.5 | 0.8 | 0.2 |
| #13 | 515 | atg-att | 73.5 | 72.5 | 71.7 | 2.5 | 2.8 | -0.5 |
| #14 | 516 A | gac-gtc | 75.6 | 71.3 | 71.4 | 0.4 | 7.0 | -0.2 |
| #15 | 516 B | gac-tac | 74.8 | 72.1 | 71.4 | 1.2 | 3.2 | -0.2 |
| #16 | 516 C | gac-ggc | 77.0 | 73.0 | 71.3 | -1.0 | 2.3 | -0.1 |
| #17 | 516 D | gac-gcc | 75.4 | 71.8 | 71.5 | 0.6 | 3.5 | -0.3 |
| #18 | 516 E | gac-ttc | 75.1 | 71.4 | 71.5 | 0.9 | 3.9 | -0.4 |
| #19 | 516 F | gac-aac | 74.9 | 72.6 | 71.2 | 1.1 | 2.7 | -0.1 |
| #20 | 517 | cag-cta | 75.2 | 67.3 | 72.0 | 0.8 | 8.0 | -0.8 |
| #21 | 518 | aac-tac | 74.9 | 70.0 | 71.7 | 1.1 | 5.3 | -0.6 |
| #22 | 522 A | tcg-ttg | 76.2 | 73.2 | 70.2 | -0.2 | 2.1 | 1.0 |
| #23 | 522 B | tcg-ccg | 75.1 | 71.9 | 72.5 | 0.9 | 3.4 | -1.3 |
| #24 | 522 C | tcg-tgg | 76.0 | 72.4 | 71.2 | 0.0 | 2.9 | -0.1 |
| #25 | 526 A | cac-tac | 76.0 | 75.2 | 65.8 | 0.0 | 0.1 | 5.4 |
| #26 | 526 B | cac-gac | 75.7 | 75.0 | 64.1 | 0.3 | 0.3 | 7.1 |
| #27 | 526 C | cac-cgc | 75.8 | 75.0 | 67.9 | 0.2 | 0.3 | 3.3 |
| #28 | 526 D | cac-ctc | 76.4 | 75.4 | 65.0 | -0.5 | -0.1 | 6.2 |
| #29 | 526 E | cac-cag | 76.3 | 75.3 | 65.1 | -0.3 | -0.1 | 6.1 |
| #30 | 526 F | cac-aac | 75.9 | 75.1 | 65.7 | 0.0 | 0.2 | 5.5 |
| #31 | 526 G | cac-tgc | 75.1 | 75.6 | 63.0 | 0.9 | -0.4 | 8.1 |
| #32 | 526 H | cac-ccc | 76.3 | 75.1 | 64.0 | -0.3 | 0.2 | 7.2 |
| #33 | 526 I | cac-acc | 76.0 | 75.2 | 62.9 | -0.1 | 0.1 | 8.3 |
| #34 | 527 | aag-agg | 76.0 | 75.2 | 67.6 | 0.0 | 0.1 | 3.6 |
| #35 | 529 | cga-caa | 76.6 | 75.3 | 65.5 | -0.6 | 0.0 | 5.7 |
| #36 | 531 A | tcg-ttg | 75.2 | 75.4 | 74.7 | 0.8 | -0.1 | -3.5 |
| #37 | 531 B | tcg-tgg | 75.5 | 75.4 | 73.8 | 0.4 | -0.2 | -2.6 |
| #38 | 531 C | tcg-gcg | 76.2 | 75.5 | 71.9 | -0.2 | -0.2 | -0.7 |
| #39 | 531 D | tcg-tac | 76.3 | 75.4 | 74.0 | -0.3 | -0.2 | -2.8 |
| #40 | 531 E | tcg-cag | 75.5 | 75.7 | 74.9 | 0.5 | -0.4 | -3.8 |
| #41 | 531 F | tcg-tag | 75.4 | 75.3 | 72.7 | 0.6 | -0.1 | -1.5 |
| #42 | 533 A | ctg-ccg | 75.6 | 75.6 | 72.1 | 0.4 | -0.3 | -1.0 |
| #43 | 533 B | ctg-atg | 74.7 | 75.6 | 73.3 | 1.3 | -0.3 | -2.1 |
| #44 | 514, 531 | ttc-ttt, tcg-ttg | 71.1 | 75.7 | 74.9 | 4.9 | -0.4 | -3.7 |
| #45 | 516, 522 | gac-ggc, tcg-ttg | 77.5 | 69.8 | 70.7 | -1.5 | 5.5 | 0.5 |

[a]Each Tm value represents an average of ten separate reactions.
*WT: Wild type RRDR sequence.

TABLE 2

Three probe Tm (° C.) code of the assay in tests of clinical *M. tuberculosis* DNA

| | | rpo1 | rpo2 | rpo3 | St. Dev1 | St. Dev2 | St. Dev3 | dTm1 | dTm2 | dTm3 | Isolates |
|---|---|---|---|---|---|---|---|---|---|---|---|
| #1 | Wild Type | 69.7 | 69.7 | 64.9 | 0.18 | 0.21 | 0.29 | — | — | — | 353 |
| #2 | 511CTG-CCG | 65.0 | 69.6 | 64.8 | 0.70 | 0.60 | 0.55 | 4.6 | 0.1 | 0.1 | 3 |
| #3 | 513CAA-CTA | 65.9 | 69.8 | 64.7 | 0.64 | 0.35 | 0.51 | 3.8 | -0.1 | 0.1 | 2 |
| #4 | 513CAA-AAA | 65.7 | 69.8 | 64.7 | 0.11 | 0.16 | 0.43 | 4.0 | -0.1 | 0.2 | 2 |
| #5 | 513-514CAA INSERTION | 64.4 | 68.9 | 64.5 | 0.00 | 0.00 | 0.00 | 5.3 | 0.8 | 0.4 | 1 |
| #6 | 516GAC-AAC | 69.8 | 67.7 | 65.1 | 0.00 | 0.00 | 0.00 | -0.1 | 2.0 | -0.2 | 1 |
| #7 | 516GAC-GTC | 69.3 | 65.4 | 64.9 | 0.44 | 0.50 | 0.49 | 0.4 | 4.3 | 0.0 | 21 |
| #8 | 516GAC-CTC | 67.6 | 62.9 | 64.5 | 0.00 | 0.00 | 0.00 | 2.1 | 6.8 | 0.4 | 1 |
| #9 | 516GAC-TAC | 68.3 | 64.7 | 64.5 | 0.36 | 0.33 | 0.87 | 1.4 | 5.0 | 0.4 | 7 |
| #10 | 518AAC DELETION | 69.8 | 62.9 | 65.3 | 0.00 | 0.00 | 0.00 | -0.1 | 6.8 | -0.4 | 1 |
| #11 | 522TCG-TTG | 69.7 | 66.8 | 64.3 | 0.00 | 0.00 | 0.00 | 0.0 | 2.8 | 0.5 | 1 |
| #12 | 526CAC-CGC | 69.8 | 69.9 | 60.0 | 0.00 | 0.20 | 0.01 | -0.2 | -0.2 | 4.9 | 4 |
| #13 | 526CAC-TGC | 69.8 | 70.1 | 59.5 | 0.00 | 0.00 | 0.00 | -0.1 | -0.4 | 5.4 | 1 |
| #14 | 526CAC-CTC | 69.8 | 69.4 | 58.9 | 0.18 | 0.50 | 0.56 | -0.2 | 0.3 | 5.9 | 3 |
| #15 | 526CAC-TAC | 69.6 | 69.6 | 59.0 | 0.34 | 0.30 | 0.14 | 0.1 | 0.1 | 5.9 | 17 |
| #16 | 526CAC-GAC | 69.8 | 69.7 | 58.3 | 0.08 | 0.44 | 0.17 | -0.1 | 0.0 | 6.5 | 4 |
| #17 | 531TCG-CAG | 69.9 | 69.9 | 68.6 | 0.01 | 0.02 | 0.06 | -0.2 | -0.2 | -3.7 | 2 |
| #18 | 531TCG-TTG | 69.8 | 69.6 | 68.6 | 0.55 | 0.53 | 0.42 | -0.1 | 0.0 | -3.7 | 147 |
| #19 | 531TCG-TGG | 70.0 | 69.9 | 67.3 | 0.00 | 0.00 | 0.00 | -0.3 | -0.2 | -2.4 | 1 |
| #20 | 533CTG-CCG | 69.8 | 69.8 | 66.1 | 0.18 | 0.14 | 0.23 | -0.1 | -0.1 | -1.2 | 10 |
| #21 | 513CAA-CTA, 523GGG-GAG | 65.8 | 68.0 | 64.4 | 0.00 | 0.00 | 0.00 | 3.9 | 1.7 | 0.5 | 1 |
| #22 | 515ATG-ATT, 516GAC-TAC | 66.7 | 64.8 | 64.4 | 0.00 | 0.00 | 0.00 | 3.0 | 4.9 | 0.5 | 1 |
| #23 | 515ATG-GTG, 516GAC-GGC | 70.2 | 66.3 | 65.1 | 0.00 | 0.00 | 0.00 | -0.5 | 3.4 | -0.2 | 1 |
| #24 | 516GAC-GGC, 518AAC-CAC | 68.5 | 59.9 | 65.4 | 0.00 | 0.00 | 0.00 | 1.2 | 9.7 | -0.5 | 1 |
| #25 | 516GAC-TAC, 531TCG-TTG | 68.2 | 64.1 | 68.3 | 0.00 | 0.00 | 0.00 | 1.5 | 5.5 | -3.4 | 1 |
| #26 | 516GAC-GGC, 533CTG-CCG | 72.2 | 67.9 | 66.2 | 0.23 | 0.19 | 0.31 | -2.5 | 1.8 | -1.4 | 2 |

St. Dev represents the +/− standard deviation of the Tm values of each of the three probes for the different clinical samples harboring the same RRDR mutations.

| Sample | Tm rpo1 | Tm rpo2 | Tm rpo3 |
|---|---|---|---|
| *M. tuberculosis* H37Rv | 69.0 | 68.9 | 64.0 |
| *M. abscessus* + Wild Type RRDR | 68.7 | 68.9 | 63.9 |
| *M. abscessus* + 516AAC | 69.0 | 66.1 | 63.4 |
| *M. abscessus* + 526CGC | 68.8 | 69.0 | 59.4 |
| *M. abscessus* + 531TTG | 69.1 | 69.3 | 68.1 |
| *M. abscessus* + 533CCG | 68.9 | 69.2 | 65.4 |
| *M. gordonae* + Wild Type RRDR | 68.8 | 68.8 | 64.0 |
| *M. gordonae* + 516AAC | 69.2 | 65.9 | 63.5 |
| *M. gordonae* + 526CGC | 68.7 | 68.9 | 59.2 |
| *M. gordonae* + 531TTG | 69.2 | 69.4 | 68.1 |
| *M. gordonae* + 533CCG | 68.8 | 69.0 | 65.3 |
| *M. chelonae* + Wild Type RRDR | 69.0 | 69.2 | 64.1 |
| *M. chelonae* + 516AAC | 68.9 | 66.1 | 63.4 |
| *M. chelonae* + 526CGC | 68.9 | 69.2 | 59.4 |
| *M. chelonae* + 531TTG | 69.1 | 69.3 | 68.1 |
| *M. chelonae* + 533CCG | 68.9 | 68.9 | 65.3 |
| *M. avium* + Wild Type RRDR | 69.1 | 69.0 | 64.0 |
| *M. avium* + 516AAC | 68.9 | 66.0 | 63.4 |
| *M. avium* + 526CGC | 68.9 | 69.0 | 59.5 |
| *M. avium* + 531TTG | 69.0 | 69.3 | 68.0 |
| *M. avium* + 533CCG | 69.0 | 69.1 | 65.4 |
| *M. kansasii* + Wild Type RRDR | 68.9 | 69.1 | 64.1 |
| *M. kansasii* + 516AAC | 68.8 | 66.0 | 63.4 |
| *M. kansasii* + 526CGC | 68.8 | 69.1 | 59.4 |
| *M. kansasii* + 531TTG | 69.1 | 69.6 | 68.0 |
| *M. kansasii* + 533CCG | 68.8 | 69.2 | 65.3 |
| *M. intracellulare* + Wild Type RRDR | 68.9 | 69.2 | 64.6 |
| *M. intracellulare* + 516AAC | 68.9 | 65.7 | 63.2 |
| *M. intracellulare* + 526CGC | 68.9 | 69.0 | 59.4 |
| *M. intracellulare* + 531TTG | 69.2 | 69.3 | 68.1 |
| *M. intracellulare* + 533CCG | 68.9 | 69.1 | 65.3 |
| *M. malmoense* + Wild Type RRDR | 69.0 | 69.1 | 64.0 |
| *M. malmoense* + 516AAC | 68.9 | 70.2-65.4 | 63.7 |
| *M. malmoense* + 526CGC | 68.9 | 69.0 | 59.5 |
| *M. malmoense* + 531TTG | 69.2 | 69.4 | 68.3 |
| *M. malmoense* + 533CCG | 68.9 | 69.1 | 65.4 |

All publications, U.S. Patents and GenBank sequences cited in this disclosure are incorporated by reference in their entireties. The citation of any references herein is not an admission that such references are prior art to the present invention.

The embodiments within the specification provide an illustration of embodiments of the invention and should not be construed to limit the scope of the invention. The skilled artisan readily recognizes that many other embodiments are encompassed by the invention. Those skilled in the art will recognize, or be able to ascertain using no more than routine experimentation, many equivalents to the specific embodiments of the invention described herein. Such equivalents are intended to be encompassed by the following embodiments.

```
SMB Probes:
SEQ ID NO. 1:
cgaccgccca tgaattggct cagctggctg gtgacggtcg        40

SEQ ID NO. 2:
ggcgcgaacc acgacagcgg gttgttctgg tccatgaacg        44
cgcc

SEQ ID NO. 3:
cgcgcgcatc accaacagtc ggtgcttgtg ggtcaacccg        44
cgcg

SEQ ID NO. 4:
cgcggccgac agttggcgct tgtgggttaa ccccgacgcc        43
gcg

SEQ ID NO. 5:
cgcgcgccgg gccccagcac caacagtcgg agcttcgcgc        41
g

SEQ ID NO. 6:
cgcggcacga cagtttgcgc ttgtgggtca accccgactg        45
ccgcg

Primers:
SEQ ID NO. 7:
agacgttgat caacatccg                               19

SEQ ID NO. 8:
acctccagcc cggcacgctc acgt                         24

SEQ ID NO. 9:
acatccggcc ggtggtcgcc                              20
```

---

The invention claimed is:

1. A method of detecting Rifampicin resistant *M. tuberculosis* in a sample comprising:
   a. amplifying a nucleic acid containing the rifampicin resistance determining region (RRDR) of the rpoB gene in a sample to provide an amplified nucleic acid;
   b. probing the amplified nucleic acid with at least three molecular beacon probes for an RRDR mutant target, wherein each molecular beacon probe comprises a sequence, which is at least 85% identical to one selected from a group consisting of SEQ ID NO:1, SEQ ID NO:2, SEQ ID NO:3, SEQ ID NO:4, SEQ ID NO:5, and SEQ ID NO:6;
   c. conducting melting temperature (Tm) analysis to determine a Tm value for each probe; and
   d. comparing the Tm value for each probe with a Tm value for a wild-type RRDR region, wherein a Tm value for at least one of the probes that is less than or greater than the Tm value for the wild-type RRDR region indicates the presence of rifampicin resistant *M. tuberculosis* in the sample.

2. The method of claim 1 wherein the nucleic acid is amplified by asymmetric PCR.

3. The method of claim 1, wherein said sample is a biological sample isolated from a subject.

4. A method of detecting Rifampicin resistant *M. tuberculosis* in a sample comprising:
   a. amplifying a nucleic acid containing the rifampicin resistance determining region (RRDR) of the rpoB gene in a sample to provide an amplified nucleic acid;
   b. probing the amplified nucleic acid with at least three molecular beacon probes for an RRDR mutant target, wherein the molecular beacon probe comprises the sequence selected from the group consisting of SEQ ID NO:1, SEQ ID NO:2, SEQ ID NO:3, SEQ ID NO:4, SEQ ID NO:5, and SEQ ID NO:6;
   c. conducting melting temperature (Tm) analysis to determine a Tm value for each probe; and
   d. comparing the Tm value for each probe with a Tm value for a wild-type RRDR region, wherein a Tm value for at least one of the probes that is less than or greater than the Tm value for the wild-type RRDR region indicates the presence of rifampicin resistant *M. tuberculosis* in the sample.

5. An isolated nucleic acid comprising a sequence which is at least 85% identical to SEQ ID NO:1, SEQ ID NO:2, SEQ ID NO:3, SEQ ID NO:4, SEQ ID NO:5, or SEQ ID NO:6.

6. A recombinant vector comprising a nucleic acid of claim 5.

7. The recombinant vector of claim 6, wherein the vector is a recombinant expression vector.

8. A host cell comprising the recombinant vector of claim 7.

9. A host cell comprising the recombinant vector of claim 6.

10. A molecular beacon probe comprising the sequence of SEQ ID NO:1, SEQ ID NO:2, SEQ ID NO:3, SEQ ID NO:4, SEQ ID NO:5, or SEQ ID NO:6 and further comprising a fluorophore attached to one end and a non-fluorescent quencher moiety attached to the other end.

11. A kit for detecting rifampicin resistant *M. tuberculosis* in a sample comprising one or more molecular beacon probes comprising a sequence which is at least 85% identical to SEQ ID NO:1, SEQ ID NO:2, SEQ ID NO:3, SEQ ID NO:4, SEQ ID NO:5, or SEQ ID NO:6.

12. The kit of claim 11 wherein the one or more molecular beacon probes comprises the sequence of SEQ ID NO:1, SEQ ID NO:2, SEQ ID NO:3, SEQ ID NO:4, SEQ ID NO:5, or SEQ ID NO:6.

13. The kit of claim 11 further comprising reagents for performing nucleic acid hybridization in a single container or separate containers, and instructions for use in a method according to claim 1.

14. The kit of claim 13 further comprising reagents for PCR.

* * * * *